United States Patent [19]

Renga et al.

[11] 4,380,636

[45] Apr. 19, 1983

[54] PROCESS FOR FORMING ESTERS (II)

[75] Inventors: James M. Renga; Pen-Chung Wang, both of Midland, Mich.

[73] Assignee: The Dow Chemical Company, Midland, Mich.

[21] Appl. No.: 387,587

[22] Filed: Jun. 11, 1982

Related U.S. Application Data

[63] Continuation-in-part of Ser. No. 295,429, Aug. 24, 1981, abandoned.

[51] Int. Cl.$^3$ ................. C07D 211/78; C07D 333/24; C07C 79/46; C07C 69/76

[52] U.S. Cl. ..................................... 546/326; 549/71; 560/20; 560/64; 560/103; 560/112; 560/122; 560/190; 560/217; 560/234; 560/261

[58] Field of Search .................... 546/326; 549/71; 560/20, 64, 103, 112, 122, 190, 217, 234, 261

[56] References Cited

U.S. PATENT DOCUMENTS 3,555,078  1/1971  Amiet et al. .................. 560/234

OTHER PUBLICATIONS

Groggins, Unit Proc. in Org. Synth., 5th ed. (1958), pp. 710–715.
Migrdichian, Org. Synth., vol. 1 (1957), pp. 328–329.
D. B. Denney, J. Org. Chem. 43, 4672 (1978).
Moore, J. Org. Chem. 44, 2425 (1979).

*Primary Examiner*—Alan Siegel
*Attorney, Agent, or Firm*—Douglas N. Deline

[57] ABSTRACT

Carboxylic acid-containing compounds are esterified by reacting at elevated temperatures with an organic ester of trichloroacetic acid and an electrophilic halide in the presence of an initiator.

14 Claims, No Drawings

PROCESS FOR FORMING ESTERS (II)

CROSS-REFERENCE TO RELATED APPLICATION

This is a continuation-in-part of copending application Ser. No. 295,429, filed Aug. 24, 1981, now abandoned.

BACKGROUND OF THE INVENTION

This invention relates to a new chemical process, more particularly to a new method of forming esters of carboxylic acids. The products obtained by the instant process are important commercial chemicals for use in polymeric, pharmaceutical and other applications.

In the past esters of carboxylic acids have been prepared by the acid-catalyzed reaction of alcohols with carboxylic acids. The process is equilibrium controlled requiring rigorous reaction conditions to drive towards completion and subsequent purification steps to remove catalyst and reactants. Methylation of acids has also been performed by reaction of the appropriate acid with diazomethane or pentamethoxyphosphorane. An alternate process is the reaction of a corresponding metal carboxylate with an organic halide thereby forming the ester. However, the reaction is hampered by formation of salt by-products.

A suitable process for forming esters of carboxylic acids which avoids the disadvantages of the prior art is desired

SUMMARY OF THE INVENTION

It has now been found that carboxylic acid-containing compounds may be easily esterified in high yields and purity by means of an acidolysis reaction with an organic ester of trichloroacetic acid at elevated temperatures in the presence of an initiator. Optionally, further ester products may be produced if an electrophilic halide esterifying agent is additionally present in the reaction mixture.

DETAILED DESCRIPTION OF THE INVENTION

The carboxylic acid-containing compounds for use according to the invention are compounds of the formula R—(COOH)$_n$ where:
n is one or two, and
R is a moiety of up to 20 carbons having valence n selected from the group consisting of aromatic carbocyclic or aromatic nitrogen-, sulfur- or oxygen-containing heterocyclic; alkyl, cycloalkyl, alkylene, cycloalkylene; and derivatives thereof containing non-interfering substituents.

By the term "non-interfering substituents" is meant substituents that do not interfere with the desired esterification reaction although such substituents may themselves be affected or modified by the reaction conditions employed. Included within the term are lower alkyl, lower alkoxy, halo, cyano, nitro, haloalkyl, aralkyl, phenoxy and hydroxy. Hydroxyl substituents in particular have been found to undergo an etherification reaction simultaneously with the esterification reaction. Despite this simultaneous ether-forming reaction, such hydroxyl substituents do not prevent the formation of esters according to the invention and they are therefore considered to be non-interfering for purposes of this invention.

Preferred carboxylic acid-containing compounds are benzoic acid and mono- or dicarboxylic acid-substituted alkanes, e.g., compounds wherein R is phenyl, alkyl or alkylene.

The organic esters of trichloroacetic acid are compounds of the formula

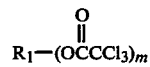

where m is one or two, and R$_1$ is a moiety of up to about 6 carbons having valence m selected from the group consisting of primary alkyl, primary alkylene, cycloalkyl and primary alkenyl. Preferred are methyl or ethyl trichloroacetate.

As previously mentioned, the carboxylic acid-containing compound is reacted with the organic ester of trichloroacetic acid thereby producing the corresponding organic ester of the carboxylic acid employed and simultaneously liberating chloroform and carbon dioxide by-products. The by-products may be distilled off as formed thereby providing a useful indication of the course of the reaction. Because the by-products may be commercially valuable, they may be collected as condensate in a suitable receiver. A stream of nitrogen or other inert purging gas may be employed to aid in removing the volatile reaction products.

Because the reaction product is highly volatile and easily separable from the reaction mixture, the instant acidolysis process is greatly improved over previously known processes in that no carboxylic acid product is produced during the course of the reaction thereby limiting the progress of the reaction to equilibrium conditions.

The products formed according to the invented process correspond to the formula

depending on the respective valences of R and R$_1$. Additionally R$_1$ of the above formula may in at least one instance be substituted by the remnant of the electrophilic halide esterifying agent when optionally present in the reaction. The formula of the product in such instances would therefore correspond to the formula

where R$_1'$ is R$_1$ or a group of up to about 20 carbons having valence m selected from the group consisting of primary alkyl, substituted primary alkyl, primary alkylene, substituted primary alkylene and substituted aryl wherein the aryl ring substituent or substituents are strongly electron-withdrawing groups located in the ortho- or para-position, provided that in at least one occurrence R$_1'$ is not R$_1$.

As previously mentioned, such alternate compounds are prepared by inclusion in the reaction mixture of an electrophilic halide esterifying compound.

Suitable electrophilic halide esterifying agents are compounds of up to about 20 carbons selected from primary alkyl halides, substituted primary alkyl halides, primary alkylene dihalides, substituted primary alkylene dihalides, and ring-substituted aromatic halides wherein the ring substituent or substituents are strongly electron-withdrawing groups located ortho or para to the halogen. These electrophilic halide compounds have the ability to substitute a primary alkyl or alkylene group, a substituted primary alkyl or alkylene group, or a ring-activated aromatic group for the organic ester group initially formed by the invented process. The substitution reaction also results in transfer of the halide resulting in formation of the corresponding organic halide from the organic ester moiety. In this embodiment of the invention, the organic ester of trichloroacetic acid is preferably methyl or ethyl trichloroacetate thereby resulting in highly volatile methyl halide or ethyl halide reaction by-products. The substitution reaction is benefited by use of elevated temperatures and removal of gaseous by-products from the reaction mixture, thereby driving the reaction towards formation of ester-substitution products. In normal operation, however, a mixture of ester reaction products occurs and the originally formed organic ester is separated from the substituted ester by standard purification methods such as distillation.

Suitable primary alkyl halides, substituted primary alkyl halides, primary alkylene dihalides, and substituted primary alkylene dihalides are compounds of up to about 20 carbons of the formula $(XCH_2)_yR''$ where X is chloro, bromo or iodo; y is one or two and where y is one, $R''$ is alkoxy, aryloxy, cyano, nitro, alkyl, aryl, aralkyl, or an alkyl, aryl or aralkyl group further substituted with alkoxy, alkoxy(poly)alkylenoxy, aryloxy, cyano or nitro groups. Where y is 2, $R''$ is the corresponding alkylene, arylene, aralkylene group or such group further substituted with alkoxy, alkoxy(poly)alkyleneoxy, aryloxy, cyano or nitro groups as above described. Preferred are those compounds wherein y is 1 and X is chloro.

Suitable aromatic halides are compounds of up to about 20 carbons of the formula $R'''—(X)_y$ where $R'''$ is an aromatic group containing at least one benzene ring structure substituted with at least one strongly electron-withdrawing group. X is chloro, bromo or iodo moiety covalently bonded to the benzene ring structure in a position ortho or para to the strongly electron-withdrawing group and y is as previously defined. Suitable strongly electron-withdrawing groups include cyano, nitro, trifluoromethyl or trichloromethyl. Preferred are those aromatic halides wherein X is chloro and y is one. Most preferred are monochlorinated benzenes containing two strongly electron-withdrawing groups present in positions ortho or para to X.

Examples of suitable electrophilic halide esterifying agents include: 1-chloropropane, 1-bromohexane, 1-chlorododecane, chloroacetonitrile, 1-chloro-2-methoxyethane, chloromethoxyethoxy methane, 1-chloro-3-nitropropane, benzyl chloride, benzyl bromide, 1-chloro-2-phenoxypropane, para-dichloromethylbenzene and the like.

Because of the increase in complexity and the need for a purification step when an electrophilic halide compound is added to the reaction mixture, the preferred embodiment of the invention is to react only the organic ester of trichloroacetic acid with the carboxylic acid-containing compound.

In the invented process, the carboxylic acid-containing compounds is contacted with the organic ester of trichloroacetic acid and optionally the electrophilic organic halide in a suitable reactor vessel. Generally, reactors of ordinary design and construction may be employed. The reactants are combined in any order and reacted at an elevated temperature from about 100° C. to about 180° C. Preferred temperatures are from about 110° C. to about 150° C. Generally, the reaction is conducted under atmospheric pressure although elevated or reduced pressures may also be employed if so desired.

The reactants may be combined in any ratio, however, generally the reactants are combined in approximately stoichiometric amounts to limit contamination of the product with unreacted starting materials. Preferred equivalent ratios of carboxylic acid-containing compound to trichloroacetic acid ester are from about 1:1 to 1:2. Where additionally an electrophilic halide is also present, some of the desired substitution product is formed regardless of the ratio of reactants employed. However, it is preferred to employ about a stoichiometric ratio of electrophilic halide and carboxylic acid-containing compound. Suitably, an equivalent ratio of carboxylic acid-containing compound to electrophilic halide of from about 1:1 to about 1:2 is employed.

The reaction is initiated by the presence of one of several suitable initiators. Basic catalysts, such as alkali metal alkoxides, salts of a strong base and a weak acid, or non-nucleophilic organic bases are suitable. The latter class consists in practice of tertiary amines, both aliphatic and aromatic. Suitable basic catalysts include triethylamine, tributylamine, pyridine, quinoline, N,N-dimethylaminopyridine, alkali metal carbonates, acetates and alkoxides. Additional suitable initiators include stable quaternary salts such as ammonium or phosphonium quaternary salts having inert counterions. Preferably, these salts have the general formula $(R'')_4AY$ where each $R''$ is a hydrocarbon moiety, A is a quaternary nitrogen or phosphorus atom, and Y is an inert (i.e., unreactive in this process) neutralizing anion which may be inorganic, e.g., chloride, bromide, iodide, bicarbonate, sulfate, or the like, or Y may be an organic ion such as formate, acetate, benzoate, phenate, or bisphenate. The $R''$ groups may be alkyl, aryl, alkaryl, aralkyl, or cycloalkyl. Also, two $R''$ groups may combine to form a heterocyclic ring. Illustrative quaternary salt catalysts are tetrabutylammonium iodide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and similar ammonium and phosphonium salts with these and other such inorganic and organic neutralizing anions as described above. The catalytic salt may be added as such to the reaction mixture or it may be formed in situ.

The quantity of initiator compound is not critical so long as any significant amount is present and available at the reaction site. Suitably from about 0.01–1 percent of initiator based on the weight of the reactants is used. Larger amounts of initiator may be employed but may complicate the ability to produce pure product.

The initiator should be at least partially soluble in the reaction mixture and it may be advantageous in accomplishing this goal to employ an additional agent to render the initiator soluble in the reaction medium. Suitable agents, referred to hereinafter as "solubilizing agents", which are particularly suitable for use with basic catalysts include the compounds generally known as phase-transfer catalysts such as, for example, cyclic oligomers of ethylene oxide known as crown ethers. Such solubilizing agents may be employed in minor amounts, for example, the ratio of about 0.005–1.0 mole per mole of basic catalyst.

A reaction solvent is usually not required or desirable, but use of a solvent may be advantageous under some conditions, e.g., when low boiling reactants or solid reaction products are involved. Excess trichloroacetic acid ester can be used as the solvent if desired. Relatively high boiling inert solvents such as N,N-dimethylformamide, sulfolane, dimethylsulfoxide, glycol diethers, and substituted aromatics such as anisole, o-dichlorobenzene, alkylated pyridines, and the like are suitable.

In the usual operation of the process the reactants and initiator are combined in a reactor as previously described. Suitably the reactor is provided with a distillation head or other means to remove the volatile reaction by-products, chloroform, carbon dioxide and optionally the organic halide formed during the course of the reaction. The by-products distill off substantially as formed and provide a useful indication of the course of the reaction. Because the by-products may themselves be commercially valuable, they may be collected as condensate in a suitable receiver. A stream of nitrogen or other inert purging gas may be employed to aid in removing volatile reaction products.

The reaction proceeds rapidly and generally is completed in from about 1 to about 5 hours depending of course on the amounts of reactants, temperature and other reaction conditions. The products are recovered from the reaction vessel and separated from residual initiator compound if desired by ordinary techniques such as distillation.

SPECIFIC EMBODIMENTS

Having described the invention, the following examples are provided as further illustrative and are not to be construed as limiting the invention.

EXAMPLE 1

A mixture of benzoic acid (1.53 g, 0.0125 mole), methyl trichloroacetate (2.22 g, 0.0125 mole), potassium carbonate (0.035 g) and 18-crown-6 cyclic polyether (0.066 g) was placed in a 25 ml round-bottom flask fitted with a stirrer, distillation head, dry ice receiver and trap. The mixture was heated with stirring to 150° C. Gas evolution was observed to begin at about 90° C. After about 3 hours, the heating was discontinued. The trap contained CHCl$_3$ (approx. 1.5 g). Distillation of the remaining mixture gave methylbenzoate identified by gas-liquid chromatography and nuclear magnetic resonance spectroscopy. Purified yield was 85 percent.

EXAMPLES 2–14

The reaction conditions of Example 1 were substantially repeated excepting that the carboxylic acids identified in Table I were employed. Purified yields of the corresponding methyl esters after gas evolution ceased are contained in Table I.

TABLE I

| Example | Carboxylic Acid | Product | % Yield |
|---|---|---|---|
| 2 | 2-methoxy benzoic acid | methyl 2-methoxy benzoate | 97 |
| 3 | 3,4-dichloro-benzoic acid | methyl 3,4-dichloro-benzoate | 90 |
| 4 | 3-methoxy-4-methyl benzoic acid | methyl 3-methoxy-4-methyl benzoate | 83 |
| 5 | 2-chloro-4-nitro benzoic acid | methyl 2-chloro-4-nitro benzoate | 81 |
| 6 | 2,6-dimethyl benzoic acid | methyl 2,6-dimethyl benzoate | 90 |
| 7 | 2-hydroxy benzoic acid* | methyl 2-methoxy benzoate | 72 |
| 8 | 2-thiophene carboxylic acid | methyl 2-thiophene carboxylate | 93 |
| 9 | 6-chloro-2-pyridine carboxylic acid | methyl 6-chloro-2-pyridine carboxylate | 83 |
| 10 | 1-hexanoic acid | methyl 1-hexanoate | 93 |
| 11 | cyclopentanoic acid | methyl cyclopentanoate | 83 |
| 12 | 3-phenyl-2-propenoic acid | methyl 3-phenyl-2-propenoate | 88 |
| 13 | succinic acid | dimetyl succinate | 75 |
| 14 | glutaric acid | dimethyl glutarate | 72 |

*Hydroxyl functionality is simultaneously methylated.

EXAMPLES 15–16

The reaction conditions of Example 1 were again substantially repeated employing different esters of trichloroacetic acid. The identity of the various reactants and the products prepared therefrom is contained in Table II.

TABLE II

| Example | Ester of Trichloroacetic Acid | Carboxylic Acid | Product | % Yield |
|---|---|---|---|---|
| 15 | ethyl trichloroacetate | 1-hexanoic acid | ethyl 1-hexanoate | 95 |
| 16 | 2-methyl-2-propenyl trichloroacetate | 1-hexanoic acid | (2-methyl-2-propenyl) 1-hexanoate | 85 |

EXAMPLES 17–18

The bis 1,2-ethylene ester of trichloroacetic acid:

was reacted with the carboxylic acids further identified in Table III. The reactants were combined in about a stoichiometric ratio under reaction conditions substantially the same as in Example 1. Results are contained in Table III.

TABLE III

| Example | Carboxylic Yield | Product | % Yield |
|---|---|---|---|
| 17 | 1-hexanoate | 1,2-ethanediyl dihexanote | 78 |
| 18 | benzoic acid | 1,2-ethanediyl dibenzoate | 70 |

EXAMPLE 19

In like manner the bis 1,2-ethylene ester of trichloroacetic acid may be reacted with terephthalic acid to give a polyester having repeating units of the formula:

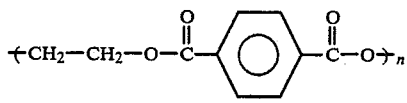

EXAMPLE 20

If the reaction conditions of Example 1 are substantially repeated excepting that the primary alkyl halide benzyl chloride is added in equal stoichiometric amount with benzoic acid and methyl trichloroacetate, the reaction product comprises a mixture of methyl benzoate and benzyl benzoate.

What is claimed is:

1. A process for preparing an ester or polyester corresponding to the formula:

wherein
m and n are one or two;
R is an aromatic or aliphatic moiety of up to 20 carbons having valence n selected from the group consisting of carbocyclic or nitrogen-, sulfur- or oxygen-containing heterocyclic aromatic groups, alkyl, cycloalkyl, alkylene or cycloalkylene groups and derivatives thereof containing noninterfering substituents;
$R_1'$ is $R_1$ or a group of up to about 20 carbons having valence m selected from the group consisting of primary alkyl, substituted primary alkyl, primary alkylene, substituted primary alkylene and substituted aryl wherein the ring substituent or substituents are electron-withdrawing groups located in the ortho- or para-position; and
$R_1$ is a moiety of up to about 6 carbons having valence m selected from the group consisting of primary alkyl, primary alkylene, cycloalkyl, and primary alkenyl,
provided that in at least one occurrence $R_1'$ is not $R_1$, comprising contacting a carboxylic acid of the formula R—$(COOH)_n$ wherein R and n are as previously defined with an organic ester of trichloroacetic acid corresponding to the formula

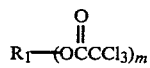

wherein $R_1$ and m are as previously defined in the presence of a catalytic amount of an initiator at a temperature from about 100° C. to about 180° C. in the presence of an electrophilic halide esterifying agent of up to about 20 carbons selected from the group consisting of primary alkyl halides, substituted primary alkyl halides, primary alkylene dihalides, substituted primary alkylene dihalides and ring-substituted aromatic halides wherein the ring substituent or substituents are strongly electron-withdrawing groups located in the ortho- or para-position and subsequently recovering the ester or polyester formed.

2. The process of claim 1 wherein the initiator comprises either a basic catalyst selected from the group consisting of alkali metal alkoxides, salts of strong bases and weak acids, and non-nucleophilic organic bases or a quaternary ammonium or phosphonium salt.

3. The process of claim 2 wherein the initiator comprises a basic catalyst and a solubilizing agent.

4. The process of claim 3 wherein the basic catalyst is an alkali metal carbonate and the solubilizing agent is a cyclic polyether.

5. The process of claim 1 wherein the temperature is from about 110° C. to about 150° C.

6. The process of claim 1 wherein R is phenyl, alkyl or alkylene.

7. The process of claim 1 wherein the organic ester of trichloroacetic acid is methyl or ethyl trichloroacetate.

8. The process of claim 1 wherein the electrophilic halide esterifying agent corresponds to the formula $(XCH_2)_yR''$ where X is chloro, bromo or iodo; y is one or two and where y is one, $R''$ is alkoxy, aryloxy, cyano, nitro, alkyl, aryl, aralkyl, or an alkyl, aryl or aralkyl group further substituted with alkoxy, alkoxy(poly)alkyleneoxy, aryloxy, cyano or nitro groups; and where y is 2, $R''$ is alkylene, arylene, aralkylene or such group further substituted with alkoxy, alkoxy(poly)alkyleneoxy, aryloxy, cyano or nitro groups.

9. The process of claim 8 wherein y is 1 and X is chloro.

10. The process of claim 9 wherein the electrophilic halide esterifying agent is benzyl chloride.

11. The process of claim 1 wherein the electrophilic halide esterifying agent corresponds to the formula $R'''(X)_y$ where $R'''$ is an aromatic group containing at least one benzene ring structure substituted with at least one strongly electron-withdrawing group, X is a chloro, bromo or iodo moiety covalently bonded to the benzene ring strcture in a position ortho or para to the strongly electron-withdrawing group and y is one or two.

12. The process of claim 11 wherein the strongly electron-withdrawing group is cyano, nitro, trifluoromethyl or trichloromethyl.

13. The process of claim 12 wherein X is chloro and y is one.

14. The process of claim 12 wherein the electrophilic halide esterifying agent is a substituted monochlorinated benzene having two strongly electron-withdrawing groups present in positions ortho or para to the chlorine.

* * * * *

UNITED STATES PATENT AND TRADEMARK OFFICE
CERTIFICATE OF CORRECTION

PATENT NO. : 4,380,636
DATED : April 19, 1983
INVENTOR(S) : James M. Renga and Pen-Chung Wang It is certified that error appears in the above—identified patent and that said Letters Patent is hereby corrected as shown below:

Column 1, line 31, "desired" should read -- desired. --.

Column 2, line 52, that portion of the formula reading "$R_1(CR)_m$ or" should read -- $R_1(OCR)_m$ or --.

Column 3, line 31, "alkoxy(poly)alkylenoxy," should read -- alkoxy(poly)alkyleneoxy, --.

Column 3, line 42, "X is chloro," should read -- X is a chloro, --.

Column 3, line 50, "two strongely" should read -- two strongly --.

Column 3, line 66, "compounds is contacted" should read -- compound is contacted --.

Column 5, line 2, "example, the ratio" should read -- example, in the ratio --.

Column 6, line 20, Table I continued under Product, "dimetyl succinate" should read -- dimethyl succinate --.

Column 6, line 60, Table III under Product, "dihexanote" should read -- dihexanoate --.

Column 7, line 21, that portion of the formula reading "$R_1'(CR)_m$ or" should read -- $R_1'(OCR)_m$ or --.

UNITED STATES PATENT AND TRADEMARK OFFICE
CERTIFICATE OF CORRECTION

PATENT NO. : 4,380,636
DATED : April 19, 1983
INVENTOR(S) : James M. Renga and Pen-Chung Wang It is certified that error appears in the above—identified patent and that said Letters Patent is hereby corrected as shown below:

Column 8, line 45, "ring strcture in" should read -- ring structure in --.

Signed and Sealed this

Sixteenth Day of August 1983

[SEAL]

Attest:

GERALD J. MOSSINGHOFF

Attesting Officer

Commissioner of Patents and Trademarks